US00PP10976P

United States Patent [19]

Roberson

[11] Patent Number: Plant 10,976

[45] Date of Patent: Jun. 22, 1999

[54] *CANNA GENERALIS* PLANT NAMED 'ROBLIBCAN'

[76] Inventor: Robert J. Roberson, 31706 E. Pink Hill Rd., Grain Valley, Jackson County, Mo. 64029

[21] Appl. No.: 08/985,237

[22] Filed: Dec. 4, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Ashwin Mehta
*Attorney, Agent, or Firm*—Rothwell, Figg, Ernst & Kurz

[57] ABSTRACT

A new and distinct cultivar of *Cannas generalis*, substantially as described and illustrated herein, characterized particularly as to novelty by its unique cantaloupe color among dwarf cannas, its apple green foliage with the ability to retain its health, vigor, and color throughout the season, its compact dwarf habit, its tendency to shed spent blooms quickly, its profuse, long term bloom display, its capacity for rhizome storage, and its slow tendency to set seed. These characteristics establish this cultivar as one well suited as a garden or pot plant, and it also has no unusual susceptibility to the traditional Canna diseases and insects.

2 Drawing Sheets

SUMMARY OF THE INVENTION

This invention relates to a new and distinct Canna cultivar which is outstanding because of it's unique cantaloupe color among dwarf cannas, its apple green foliage with the ability to retain its health, vitgor, and color throughout the season, its compact dwarf growth habit, its tendency to shed spent blooms quickly, its profuse, long-term bloom display, its capacity for rhizome storage, and its slow tendency to set seed. This selection was made from a specially designed Canna hybridizing program with said hybrid cultivars being planted and grown in Grain Valley, Mo.

ORIGIN AND ASEXUAL REPRODUCTION

Asexual reproduction of this cultivar by dividing the rhizome was directed by me, such reproduction establishing that the plant does in fact maintain the characteristics described, in successive generations.

It should be noted that the plant was initially selected from a Canna planting being grown near Grain Valley, Mo. in a cultivated area and has since been reproduced by dividing the rhizome in the vicinity of Grain Valley, Mo. with the new and distinct characteristics stated herein, found to be maintained through successive generations as before recited.

*Canna generalis* is a group of tropical to sub-tropical herbaceous plants grown primarily for their rapid growth and vivid, flamboyant, summer blooms. They are grown in USDA zones 9–10 as a perennial and in USDA zones 3–8 as an annual. General growth habit includes an erect central (main) stalk with large tropical alternate leaves. This massive plant, usually 24"–96" in height, is topped by a colorful, inflourescent display. They are of easy cultivation in any fertile, moist soil, especially soils high in humus.

This cultivar of *Canna generalis* 'Roblibcan' may further be described as having a number of distinctive characteristics which are enumerated in the succeeding specific description but broadly stated as comprising a unique cantaloupe color among dwarf cannas, apple green foliage with the ability to retain it's health, vigor, and color throughout the season, compact dwarf growth habit, tendency to shed spent blooms quickly, profuse, long-term bloom display, good capacity for rhizome storage, and slow tendency to set seed. The floral display is melon (PMS#162) with pale yellow (PMS#106) in the throat and emerging slightly onto the base of the petals. The bloom period begins at approximately twelve weeks after planting and continues until frost.

I have chosen to identify this new cultivar as *Canna generalis* 'Roblibcan'. This cultivar is being marketed in the United States under the name of LIBERTY (™) CANTALOPE.

BRIEF DESCRIPTION OF THE DRAWING

The accompanying photograph shows as nearly true as it is reasonably possible to make the same, in a color illustration of this character, typical flowers and leaves of the new variety. The photographic drawing illustrates the flower form, the novel and distinctive melon colored flowers, and the green foliage.

In the photograph.

DETAILED DESCRIPTION

Figure 1:
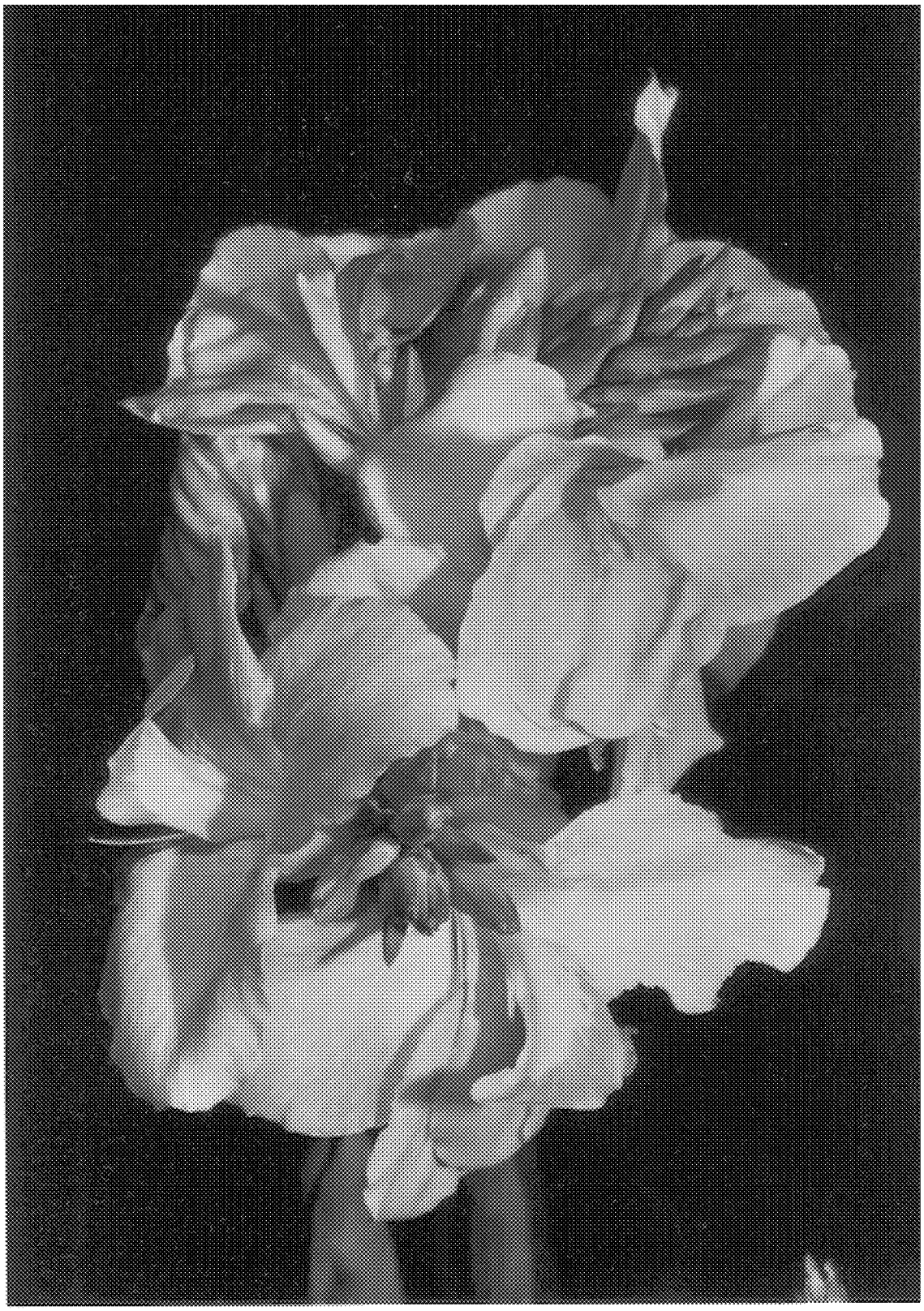
FIG. 1 illustrates the mature flower.
Figure 2:
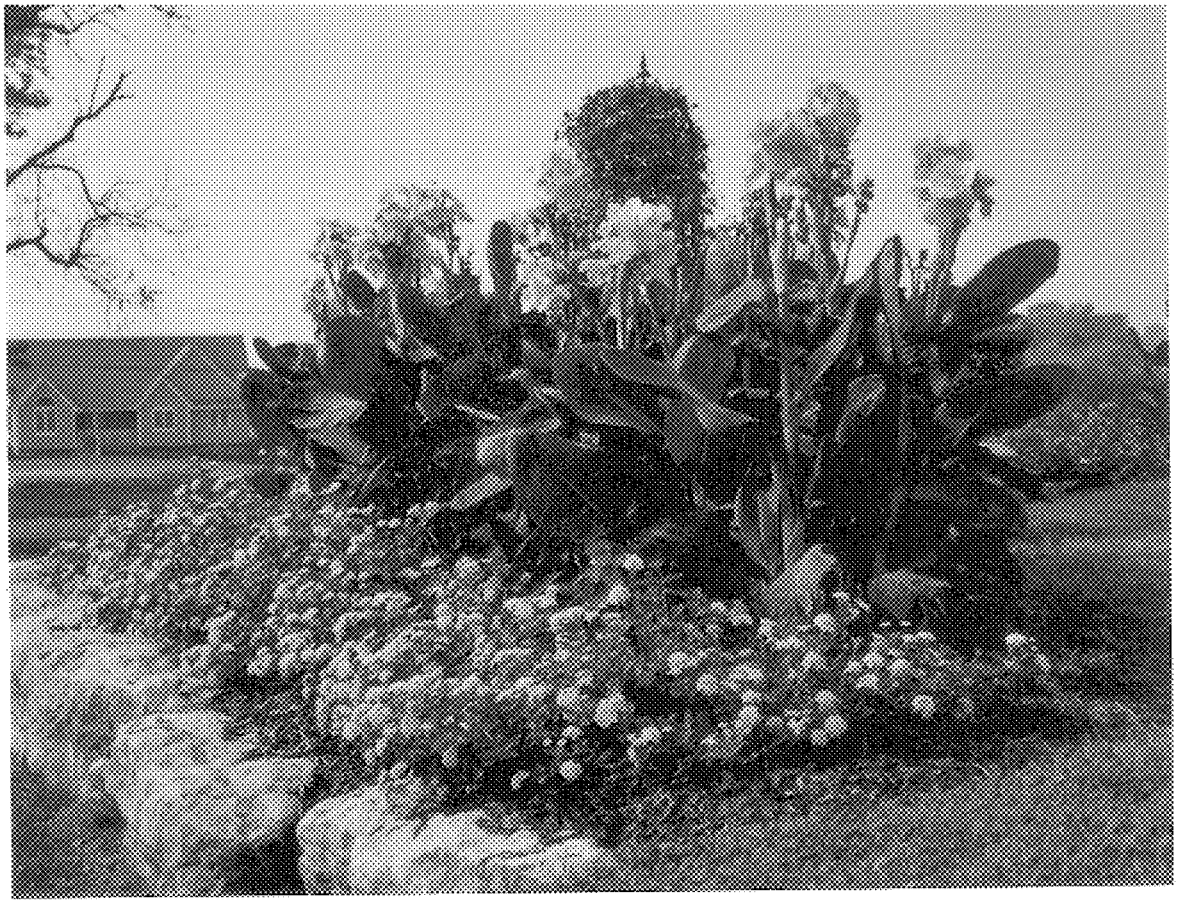
FIG. 2 illustrates the whole plant.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo., unless stated otherwise.

Parentage:

*Seed parent.*—*Canna generalis* hybrid 'Angel Pink', self pollinated.

Propagation: Asexual reproduction by rhizome division started near Grain Valley, Mo.

Plant descriptions:

*Inflorescence and reproductive parts.*—The overall inflorescence is thrysoid (mixed) and is approximately 25 cm in length by 15 cm in width when mature. The terminal axis is indeterminate and the lateral axis are cymose and determinate. The large, zygomorphic, hermaphrodite flowers are borne terminally and more or less erect in a racemose inflorescence and are of anthesis together with one that is in bud. The flowers, borne on short pedicels occur in pairs forming a two-flowered cincinnus. Each flower is subtended by a bract. The outer whorl of he perianth consists of three free, imbricate sepals, the inner whorl of three basically united petals. There are typically three to five petaloid staminodes (showy portion of inflorescence) with the smaller fertile petaloid stamen and style visible at the center of the flower. Colors of "Petals" (showy portion composed of petaloid staminodes): are predominately melon (PMS #162) with pale yellow (PMS 102) in the throat and emerging upon to the segments. Due to the unusual composition of the reproductive parts, self pollination is more common in cannas than in cross pollination. The petaloid stamen and style are visible at the center of the flower. The stamen can be recognized by the presence of the single anther-cell along its upper margin. The pistil is made up of the stigma or tip, the petaloid style and a three locular ovary. The ovary is borne on a short pedicel and each loculus contains numerous anatropous ovules attached to an axile placenta. The rarely formed capsule has a warty pericarp that disintegrates at maturity to release the seeds.

*Fragrance*.—None detected.

*Terminal axis*.—Indeterminate.

*Lateral axis*.—Cymose and determinate.

*Petaloid staminodes*.—Melon (#162) with pale yellow (#102 tips.

*Perianth segments*.—Predominately PMS #162 with pale yellow (#102) in the throat.

*Bud at approximately one week prior to opening*.—5.2 cm to 7.1 cm which is comprised of: Sepal — 0.7 cm to 1.4 cm; Petal — 2.1 cm to 3.2 cm; and Emerging stamenodes — Varying from 1.6 cm to 4.1 cm.

Color of reproductive parts:

*Anther*.—Dark brown(PMS#471) to black at dehiscence.

*Stigma*.—Translucent cream.

*Ovary*.—Medium green (PMS#361).

*Stamen*.—Melon and yellow blend, similar to inflorescence.

*Style*.—Melon and yellow blend.

*Seeds*.—At maturity are black, and approximately 4 mm by 7 mm in size.

Leaves: The alternate leaves are long ovate in shape and have pinnate veins and a dominate mid-rib. The are large, broad, simple, and entire with sheathing petioles. The average size of leaves at maturity is 52 cm in length and 28 cm in width. The dominate color in young leaves is pale green (PMS#366) on both front and back with a transition to medium green (PMS#362) on both front and back at maturity.

Tubers (rhizomes): These tuberous rhizomes are a bone-whiter when immature, and transitions into a darker cream at maturity. The rhizomes are covered by papery scale-like leaves. This papery-like layering is (PMS #439) with darker veining (PMS #440). tThe average rhizome is 8 cm in length and 2.3 cm in width.

Roots: The fleshy roots arise from the internodes of the rhizomes and vary from 1–3 mm in diameter and are an average length of 28 cm.

Flowering time: The bloom period begins at approximately twelve weeks after planting (when planted at the recommended season and given reasonable care) and continues until frost. No pruning or pinching is required for optimum flowering performance. Spent blooms are shed quickly (approximately 30 hours after opening).

Diseases: No known unusual susceptibility to diseases noted to date.

Insects: No unusual susceptibility to insects noted to date.

General Observations

*Canna generalis* 'Roblibcan' with its unique cantaloupe color among dwarf cannas, its apple green foliage with the ability to retain its health, vigor and color throughout the season, its compact dwarf growth habit, its tendency to shed spent blooms quickly, its profuse, long-term bloom display, its capacity for rhizome storage, and its slow tendency to set seed is striking in beauty, cleanliness, and dependability in the garden and landscape.

For the purpose of ornamental horticulture in our present living environments which include smaller yards and patio gardening, 'Roblibcan' is ideal due to several characteristics. These plant characteristics are:

A. Colors of Inflorescence and leaves: The carrying power (visibility) of this cultivar's melon inflorescence contrast the rich green foliage for a striking landscape display.

B. Dwarf stature: In today's market, this is in extremely high demand. The dwarf height (3½ feet) along with overall plant balance, qualifies this as an optimum landscape Canna.

C. Compact growth: Another goal was to achieve growth habit in a cultivar displaying the new melon color blooms. The achievement of this growth habit is primarily shown by two characteristics: The stem thickness and the internode spacing.

For example, in this Canna, the stem thickness (1.4") to average height (42") ratio is 1 to 30. In the comparison plant, Stadt Felbach, the stem thickness (1.5) to height (54") is 1 to 36. The internode spacing of Stadt Felbach is 8.6" and the internode spacing of "Roblibcan" is 7.1" which creates a more dense, compact presentation.

D. Self Cleaning: Professionals in today's nursery industry have an increasingly high level of plant acquisition specifications. This self cleaning (shedding spent blooms quickly) characteristic is considered very desirable for assuring an optimum appearance in the garden or landscape planting.

E. Winter Storage: The storage capability of 'Roblibcan' is another characteristic that renders this cultivar advantageous both to home gardeners and to commercial growers. The rhizomes are superior for storage because an average of 90% of stored rhizomes are viable after the winter storage period.

The winter storage capability of 'Roblibcan' is very important for two reasons. Since cannas are only grown as perennials in USDA zones 9–10 and must be dug and stored in zones 3–8, a vast majority of home gardeners must routinely dig and store the rhizomes during the winter months. There is great variance as to the ability of different varieties to store successfully. 'Roblibcan' survives winter storage with a high rate of success. Secondly, this storage ability of 'Roblibcan' is of great advantage to commercial canna growers in USDA zones where the cannas must be dug and stored over winter months and a high degree of plant loss renders the product of no marketable value.

Comparison to Known Varieties

The cultivar may be compared with known varieties along the following lines.

*Canna generalis* 'Stadt Felbach' is an appropriate choice for a comparison to *Canna generalis* 'Roblibcan' because of their similar bloom and folage color. 'Roblibcan' however, is an improved cultivar due to three characteristics: (1) It has a more dwarf height, i.e., 3½ feet compared to a height of 4½ feet for 'Stadt Felbach'; (2) 'Roblibcan' maintains a cleaner presentation in the garden as it sheds its spent blooms more quickly than 'Stadt Felbach'; and (3) 'Roblibcan' has blooms that are of a cleaner, clearer color than that of 'Stadt Felbach'.

*Canna generalis* 'Angel Pink' is the seed parent of 'Roblibcan'. There are two primary observed differences between these two cultivars. 'Angel Pink' is a rose pink as compared to the instant variety's color of cantaloupe. Additionally, 'Angel Pink' is approximately 10 inches shorter than 'Roblibcan'.

I claim:

1. The new and distinct cultivar of Canna plant, substantially as described and illustrated herein, characterized particulary as to novelty by its unique cantaloupe color among dwarf cannas, its apple green foliage with the ability to retain its health, vigor, and color throughout the season, its compact dwarf habit, its tendency to shed spent blooms quickly, its profuse, long term bloom display, its capacity for rhizome storage, and its slow tendency to set seed.

* * * * *